Figure 1:
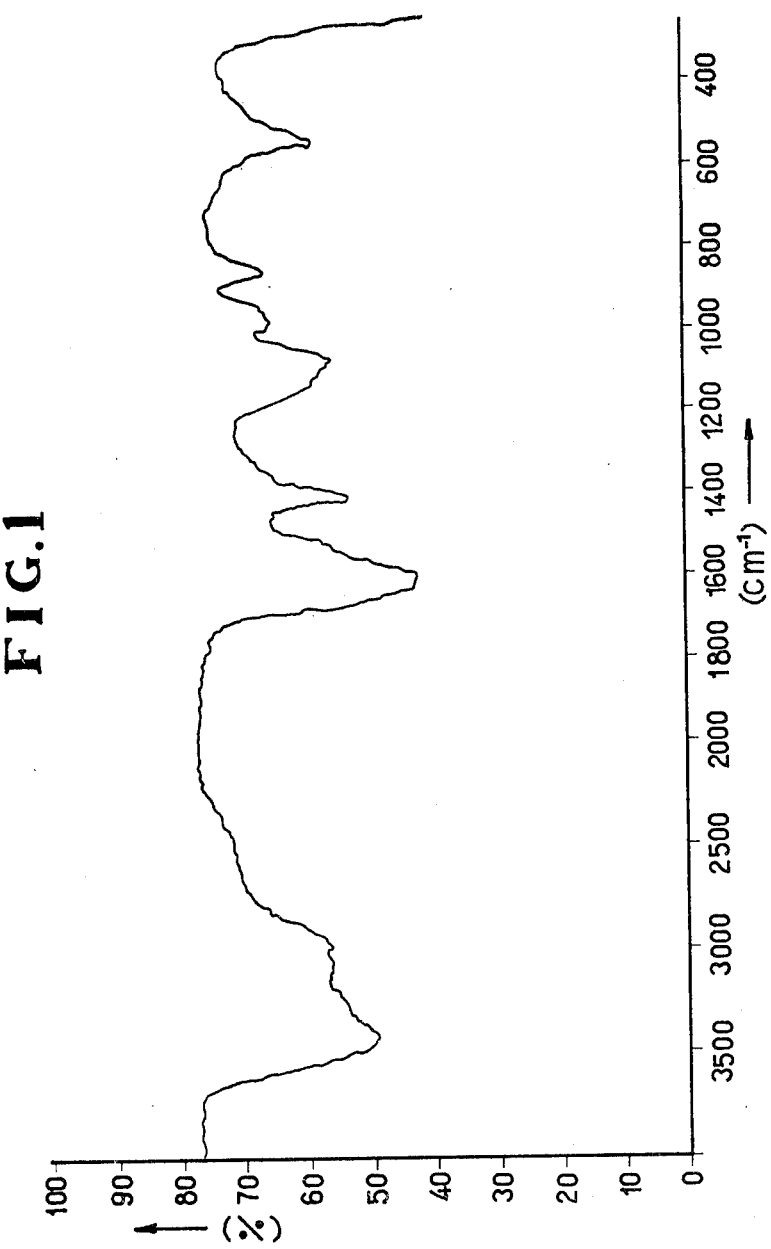

United States Patent [19]

Suzuki et al.

[11] Patent Number: 4,482,543

[45] Date of Patent: Nov. 13, 1984

[54] BIOLOGICALLY ACTIVE SUBSTANCE, PROCESS FOR PREPARING THE SUBSTANCE AND IMMUNOACTIVE COMPOSITION

[75] Inventors: Naoyoshi Suzuki, Tokyo; Tsuneo Hirose, Obihiro; Humio Osaki, Tokushima, all of Japan

[73] Assignee: Otsuka Pharmaceutical Factory, Inc., Naruto, Japan

[21] Appl. No.: 349,608

[22] Filed: Feb. 17, 1982

[30] Foreign Application Priority Data

Feb. 27, 1981 [JP] Japan .................................. 56-28553
Feb. 27, 1981 [JP] Japan .................................. 56-28554

[51] Int. Cl.³ .................... C07C 103/52; A61K 37/02
[52] U.S. Cl. ............................. 424/177; 260/112.5 R
[58] Field of Search ................ 424/177; 260/112.5 R, 260/112 R

[56] References Cited

U.S. PATENT DOCUMENTS 4,202,969  5/1980  Ueno et al. ......................... 424/181
4,235,771  11/1980 Adam et al. .................. 260/112.5 R

FOREIGN PATENT DOCUMENTS 2078229  1/1982  United Kingdom .

OTHER PUBLICATIONS

Igaraski, Zbl. Bakt. Hyg., I. Abt. Orig., A224, 374–382, (1979).
Nagasawa et al., Immunobiol., 157, 307–309, (1980).

*Primary Examiner*—Delbert R. Phillips
*Assistant Examiner*—F. T. Moezie
*Attorney, Agent, or Firm*—Larson and Taylor

[57] ABSTRACT

This invention relates to a biologically active substance which is a glycoprotein having a molecular weight of 3,000 to 5,000 and has activity to inhibit toxoplasma multiplication in homologous cells and heterologous cells.

This invention also relates to a process for preparing the substance, immunoactive compositions containing the substance and use of the substance as a drug.

10 Claims, 3 Drawing Figures

BIOLOGICALLY ACTIVE SUBSTANCE, PROCESS FOR PREPARING THE SUBSTANCE AND IMMUNOACTIVE COMPOSITION

The present invention relates to a novel biologically active substance, a process for preparing the substance, immunoactive compositions containing the substance and use of the substance as a drug.

It has recently been found that the circulating blood of toxoplasma-hyperimmune animals contains mediators which inhibit the multiplication of toxoplasma in normal cells of the animal. It has also been found that when spleen cells of the toxoplasma-hyperimmune animal are cultured in the presence of a specific antigen, such as toxoplasma lysate antigen (hereinafter referred to as "TLA"), or a non-specific mitogen, such as concanavalin A (hereinafter referred to as "Con A") or phytohemagglutinin (hereinafter referred to as "PHA"), the supernatant of the resulting culture contains factors which inhibit multiplication of toxoplasma in homologous cells (Igarashi I., Zbl. Bakt. Hyg., J. Abt. Orig. A244, 374–382, 1979; Shirahata T., et al., Z. Parasiteik., 53, 31–40, 1977; and Nagasawa et al., Immunobiology, 157, 307–319, 1980).

The toxoplasma multiplication inhibitory factor is a protein which appears to be a T-lymphocyte-producing substance and which has a molecular weight of about 30,000 to about 40,000. The factor, which is termed "Toxo-GIF," inhibits toxoplasma multiplication in homologous cells only but is unable to exhibit substantial inhibitory activity in heterologous cells, thus showing species specificity. Accordingly the factor is not usable for preventing or curing toxoplasmosis in man and/or animals other than the infected host.

An object of the invention is to provide a novel biologically active substance having no species specificity but possessing immunoactivity to inhibit toxoplasma multiplication also in heterologous cells.

Another object of the invention is to provide a biologically active substance having immunoactivity to inhibit multiplication of not only toxoplasma but also the other protozoans, viruses, bacteria and like microorganisms and mouse leukemia P388 cancer cells.

Another object of the invention is to provide a process for preparing the novel biologically active substance.

Another object of the invention is to provide drugs, namely immunoactive compositions, especially protozoacidal, bactericidal and virucidal compositions which contain the biologically active substance.

Still another object of the invention is to provide a method of preventing and curing infections in man and animals with use of the immunoactive composition.

These and other objects of the invention will become apparent from the following description.

More specifically the present invention provides a novel biologically active substance characterized in that the substance is a glycoprotein having a molecular weight of 3,000 to 5,000 as determined by a gel filtration method and has activity to inhibit toxoplasma multiplication in heterologous cells as well as homologous cells, a process for preparing the substance and immunoactive compositions containing the substance.

The biologically active substance of the invention has the following physical and chemical properties and structural features.

(1) Molecular weight

The substance of this invention is found to have a molecular weight of 3,000 to 5,000 by a gel filtration method. The method is carried out by using Sephadex G-100 (crosslinked dextran gel, produced by Pharmacia Co., Uppsala, Sweden), Toyopearl HW-40 or HW-50 (polyvinyl-type gel, produced by Toyo Soda Co., Ltd., Japan) and Sephacryl S-200 (crosslinked allyldextran gel, produced by Pharmacia Co., Uppsala, Sweden), and the molecular weight is determined by the elution pattern as compared with those of known substances. The molecular weight determined by another gel filtration method using Sephacryl S-200 and Sephadex G-15 (crosslinked dextran gel, produced by Pharmacia Co., Uppsala, Sweden) also ranges from 3,000 to 5,000.

(2) Solubility in water

The substance is freely soluble in water (according to the Japanese Pharmacopoeia, 10th Rev., Rule 22).

(3) Solubility in organic solvents

According to the Japanese Pharmacopoeia, 10th Rev., Rule 22, the substance is practically insoluble in methanol, ethanol, ether, benzene, chloroform and acetone.

(4) Ratio of sugar and protein contents

The present substance comprises glycides chiefly including hexose and hexosamine. The hexose content is determined by the phenol-sulfuric acid reaction, the hexosamine content by the Elson-Morgan's procedure, and the protein content by a total nitrogen measuring device, Model MCI TN-02 (product of Mitsubishi Kasei Co., Ltd., Japan). The result (W/W %) is as follows.

| | |
|---|---|
| Protein | 85–90 W/W % |
| Hexosamine | 9–13 W/W % |
| Hexose (calcd. as glucose) | 1–2 W/W % |

(5) pH

One W/V % aqueous solution of the present substance has a pH of 7.0 to 7.2.

(6) Thermal stability

One W/V % aqueous solution of the present substance, even when heated at 60±0.1° C. for 30 minutes, still retains the immunoactivity and activity of inhibit toxoplasma multiplication in homologous cells and heterologous cells.

(7) IR absorption spectroscopy

FIG. 1 shows an IR analysis diagram determined with use of KBr tablet. The diagram reveals the following characteristic absorption values (cm$^{-1}$).

3600–2900 (strong), 1700–1500 (strong), 1440–1380 (medium), 1160–1080 (medium), 550 (medium)

(8) UV absorption spectroscopy

Figure 2:
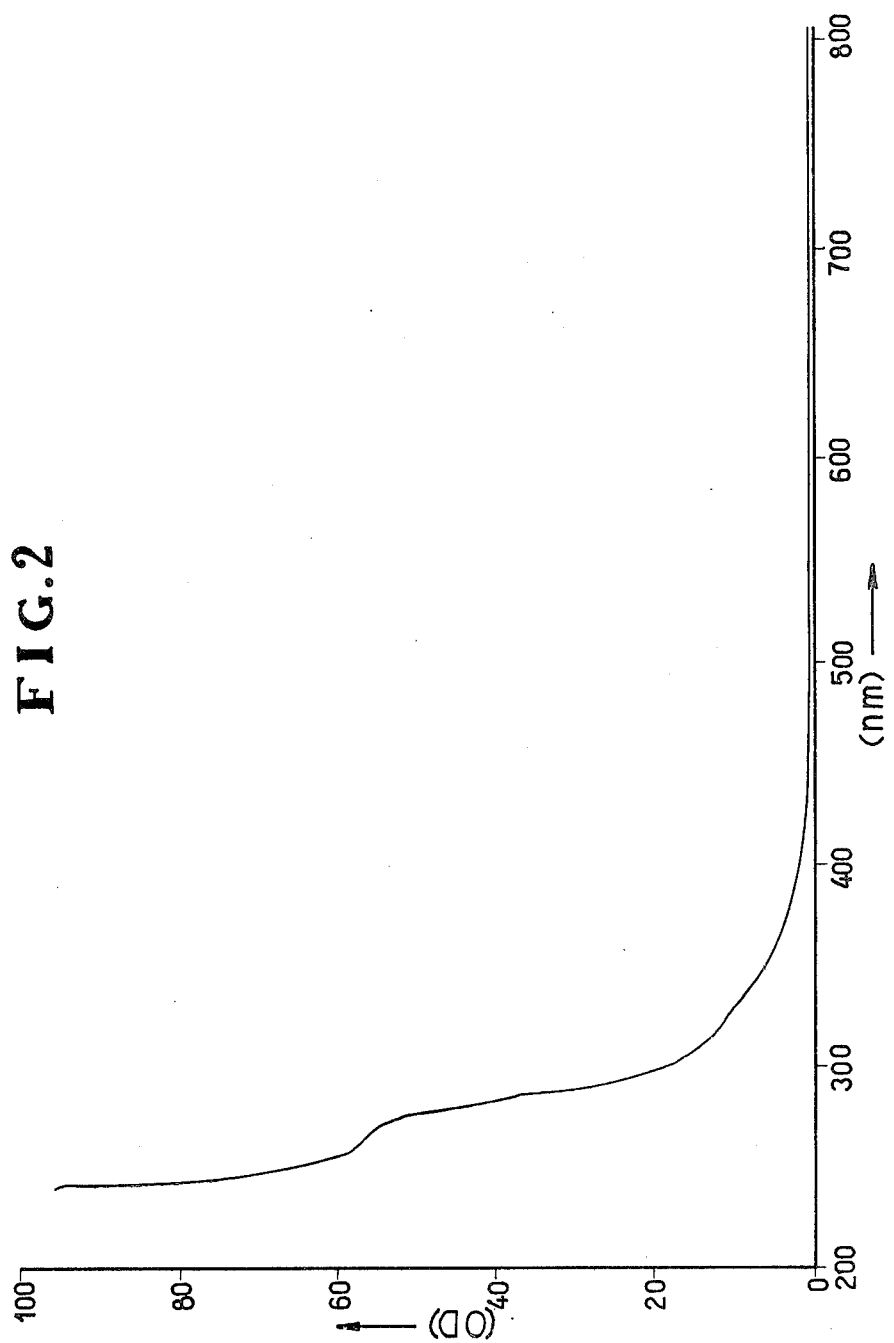

FIG. 2 is a UV analysis diagram determined by a 1-cm cuvette cell for a 0.1 W/V% aqueous solution of the present substance. The diagram shows maximum absorption at 274–276 nm.

(9) Color reactions

A 0.1 W/V% aqueous solution of the present substances is tested for color reactions with the following results.

| | |
|---|---|
| Lowry-Folin process (peptide linkage): | positive |
| Ninhydrin reaction (amino acid): | positive |
| Phenol-sulfuric acid reaction (saccharide): | positive |
| Elson-Morgan's reaction (amino-sugar): | positive |

(10) Color and appearance

White and amorphous.

(11) Constituent amino acids

The protein portion of the substance comprises aspartic acid, threonine, serine, glutamic acid, glycine, alanine, cystine, valine, methionine, isoleucine, leucine, tyrosine, phenylalanine, lysine, tryptophan, histidine, arginine and proline. These amino acids are detected by using an amino acid analyzer (The Neubauer-Rhode reaction method [Japanese Pharmacopoeia, 10th Rev., C-1108 (1981)] is used for tryptophan.) Of these constituent amino acids, the aspartic acid, glutamic acid and lysine contents are peculiarly large. An analysis by an amino acid analyzer has revealed that the contents of these three components account for 45 to 65% of the total amino acid content.

The substance of this invention is further characterized by its unique activity to inhibit toxoplasma multiplication in heterologous cells as well as in homologous cells. The activity to inhibit toxoplasma multiplication in heterologous cells refers to the activity to inhibit toxoplasma multiplication in cells of mammals different in kind from the mammal used for preparing the present substance. This activity will become apparent from the tests to be described later. Already known are proteins, such as Toxo-GIF, which inhibit toxoplasma multiplication in homologous cells (i.e. substances which inhibit toxoplasma multiplication in cells of animals of the same species as the mammal used for the production of the substance), but such a substance, unlike the present substance, has species specificity, is unable to inhibit toxoplasma multiplication in heterologous cells and has a molecular weight of about 30,000 to about 40,000. Thus the known substance distinctly differs from the substance of the invention. In fact, the presence of any substance is not known which inhibits toxoplasma multiplication in heterologous cells; the glycoprotein having the above activity and a molecular weight of 3,000 to 5,000 has been discovered by us for the first time.

The present substance having the foregoing physicochemical properties, structural features and biological properties inhibits toxoplasma multiplication and is useful as a toxoplasmacidal agent for man and other mammals. Our research has further revealed that the present substance is active not only on toxoplasma but also on the other protozoans and various bacteria, such as gram-positive bacteria of the species Micrococcus, Bacillus, etc. and gram-negative bacteria of the species Escherichia, Proteus, etc. and viruses in inhibiting the multiplication of such microorganisms in cells. The substance is further found to possess activity (immunoactivity) to inhibit the multiplication of mouse leukemia P388 cancer cells. Accordingly the present substance is useful as an agent for preventing and curing infections of normal mammals with these microorganisms (i.e. for toxoplasmacidal, bactericidal and virucidal applications). The invention therefore provides immunoactive compositions as such drugs and a method of using the compositions.

The process for preparing the present substance will be described below.

Basically the substance is prepared by causing an enzyme to act on a starting material obtained from the blood or cells of various mammals. More specifically the present substance is prepared by causing a proteolytic enzyme to act on at least one starting material selected from the group consisting of (A) the blood plasma or serum obtained from a mammal hyperimmunized with protozoa such as toxoplasma, (B) the supernatant of a culture of spleen cells from a mammal hyperimmunized with protozoa such as toxoplasma, and (C) the supernatant of a culture of spleen cells from a normal mammal incubated in the presence of at least one of the supernatant (B), a specific antigen, heating the resulting product to inactivate the enzyme, and separating a biologically active substance from the product. Preferably, the product resulting from the proteolysis is hydrolyzed before the heating.

The blood plasma or serum (A) useful as the starting material is produced by a known method. For example, it is prepared by collecting the blood from a mammal hyperimmunized with protozoa in accordance with one of the methods disclosed in the foregoing literature. Examples of useful mammals are a mouse, dog, ox or cow, horse, goat, sheep, rabbit, swine and various other mammals. Among these mammals, mouse, dog and bovine are especially preferable. The kind of protozoa to be used is not particularly limited. However, it is preferable to use Sporozoa, especially Toxoplasma such as *Toxoplasma gondii*, Haemosporidia such as *Plasmodium berghei* NK strain, and Piroplasmea such as *Babesia gibsoni*, *Babesia rhodhaini*, *Babesia ovata* and *Babesia sergenti*.

According to the present invention, even when inoculating any one species of the foregoing mammals with any one kind of the protozoans, a substance is prepared which has immunoactivity to inhibit multiplication of the other kinds of protozoans as well as the one applied for inoculation in cells of not only the same species as the mammal inoculated therewith but also the other species. For example, a substance prepared in accordance with this invention by inoculation of *Toxoplasma gondii* in mice is immunoactive to inhibit the multiplication of Toxoplasma, Plasmodium and other protozoans, in cells of mouse, dog, bovine and various other mammals.

The mammal can be hyperimmunized with protozoa merely by inoculating the mammal therewith. The inoculation can be carried out intraperitoneally, intravenously or orally. The amount of protozoans to be applied for inoculation is not particularly limited but is variable according to the kind of the mammals as well as of the protozoans and the method of inoculation. It is usually about $10^2$ to about $10^8$ protozoans per mammal. The inoculation can be conducted dividedly, usually two to three times. Preferably the mammal is inoculated, for example, with about $10^2$ to about $10^8$ protozoans first and subsequently with about $10^4$ to $10^8$ protozoans a suitable period of time thereafter, usually in the third to tenth week after the first inoculation.

According to the preferred method, the mammal is hyperimmunized by inoculating with protozoa and thereafter inoculating with a specific antigen and/or a non-specific mitogen. The term "specific antigen" used herein refers to an antigen derived from a protozoa and having specificity to the protozoa. Specific antigens usable in the present process are different from protozoa to protozoa for the process concerned. For example, if toxoplasma is used as the protozoa, TLA is usable as the specific antigen. In the case of Plasmodium and Babesia involved, useful specific antigens are Plasmodium lysate antigen (hereinafter referred to as "MLA") and Babesia lysate antigen (hereinafter referred to as "BLA"), respectively. These specific antigens are all known and obtained for example by treating the protozoa with an ultrasonic vibrator and centrifuging the mixture to separate aqueous fragments therefrom [see, Jacobs, L. and M. N. Lunde, J. Parasitol., 43, 308–314 (1957), and Ishimine, T., et al., Jap. J. vet. Sci., 41, 487–493 (1979)]. The term "non-specific mitogen" is used herein to mean a lectin which causes blastoid transformation of lymphocytes. Typical of such non-specific mitogens are Con A, PHA, etc. The specific antigen or non-specific mitogen is applied usually several to ten-odd weeks after the incubation with the protozoans. It is preferable to conduct the inoculation of the protozoans dividedly twice or more and to apply the specific antigen or non-specific mitogen in the 1st to 5th week, preferably approximately in the second week, after the final inoculation of the protozoans. The specific antigen or non-specific mitogen is applied intravenously in an amount of about 5 to about 150 μg per kg of the body weight of the mammal. The method, amount and time of inoculation are of course suitably determined in accordance with the kind of the specific antigen and/or non-specific mitogen, the kind of mammal, etc. The mammal is hyperimmunized with protozoa usually ten-odd to several tens-odd days after the final inoculation of the protozoa, or at least 24 hours after the specific antigen or non-specific mitogen is given. The blood plasma or serum can be separated from the mammal in a conventional manner. Thus the plasma or serum to be used as one of the starting materials of this invention is obtained.

The supernatant of culture (B) useful as a starting material of the invention is prepared preferably by the following method.

First, a mammal hyperimmunized with protozoa is prepared by the same method as described above and the spleen is removed from the mammal. Spleen cells are separated off according to the Conray-Ficoll method [Immunol. Cell., 1, 265–268 (1971), Tsuji]. The spleen cells are washed by centrifugation with heparinized Hanks balanced salt solution containing 10 units heparin/ml [Modern Biology Series 23, "Method of Incubating Animal Cells", by Yukiaki Kuroda, Kyoritsu Shuppan, Japan, 1974, hereinafter referred to as "heparinized HBSS"]. The resulting precipitate is then suspended in TC-199 medium [see, "Igaku to Ayumi (Progress of Medicine)", 62, No. 6, Aug. 5, 1967], whereby the medium is adapted to contain about $10^4$ to about $10^8$ cells/ml. The TC-199 medium used as above has added thereto 5 to 20 W/V % of heat-inactivated calf serum (hereinafter referred to as "HICS") and antibiotics (preferably 100 units penicillin G and 100 μg dihydrostreptomycin per ml of the medium). To the medium is added about 5 to about 150 μg/ml, preferably about 80 to about 120 μg/ml, of a specific antigen and/or non-specific mitogen, and the medium is maintained for incubation at about 37° C. for about 1 to about 2 days, preferably for about 48 hours, in the presence of carbon dioxide gas. The specific antigen and non-specific mitogen used in this method are the same as used in the above method of preparing the blood plasma or serum (A). The medium is thereafter centrifuged to collect a supernatant. Thus the supernatant of spleen cell culture of the hyperimmunized mammal is obtained for use as a starting material of the invention.

The supernatant of culture (C) is prepared, for example, by the following method. In the same manner as described for (B), spleen cells are separated from a normal manner, and the cells are washed by centrifugation with heparinized HBSS and suspended in TC-199 medium containing HICS and antibiotics. To the medium is then added the supernatant (B) in a proportion of 60 to 70 V/V %, or a specific antigen in an amount of about 5 to about 150 μg/ml, preferably about 80 to about 120 μg/ml. In this method, the same specific antigen described above concerning (A) are also usable. The supernatant may be used conjointly with the specific antigen. The cells are cultured at 37° C. for about 3 weeks. In the meantime, about ⅓ of the medium is replaced by the fresh medium preferably every three days. After the completion of incubation, the medium is washed with heparinized HBSS. A specific antigen and/or non-specific mitogen is then added again to the medium in an amount of about 5 to about 150 μg/ml, preferably about 80 to about 120 μg/ml. The medium is maintained for further incubation at 37° C. for 1 to 2 days, preferably for about 48 hours, in the presence of carbon dioxide gas. The supernatant of spleen cell culture of the normal mammal is obtained by thereafter following the same procedure as for (B).

The substance of this invention is obtained by causing a proteolytic enzyme to act on the starting material (A), (B) or (C), hydrolyzing the resulting product when so desired, heating the product to in-activate the enzyme and subjecting the resulting product to separation and purification by suitable means.

Examples of useful proteolytic enzymes are usual proteinase, i.e., endopeptidases, exopeptidases and endo- and exo-peptidases, including pronase, papain, chymotrypsin, trypsin, aminopeptidase, carboxypeptidase, etc. These enzymes are usable singly or in admixture. Of these, pronase, papain and chymotrypsin are preferable, among which pronase is the most preferable. For the enzymatic treatment of the starting material, usually about 0.01 to about 0.1 W/V % of the enzyme is used. The treatment is conducted at a temperature and a pH which are suitable for the enzyme used. For example when pronase is used, the treatment is conducted at a temperature of about 36° to about 38° C. at a pH of about 7 to about 8. The treatment is completed when the desired substance is obtained in a maximum yield, usually in about 6 to about 24 hours.

The product resulting from the proteolysis is then subjected to heat-treatment thereby inactivating the enzyme. The heat treatment is conducted, for example, by heating the product at a temperature of about 95° to about 100° C. for about 1 hour. The heat treatment also serves to sterilize and activate the desired substance and to remove by decomposition unenzymolyzed substances or specific antigen of heterologous cells which is likely to be present in the enzyme-treated product. The product resulting from the proteolysis can be subjected to hydrolysis before the heat-treatment, if desired. The hydrolysis is preferably conducted for the decomposition of the unenzymolyzed substances. It is carried out usually with use of sodium hydroxide, potassium hydroxide or like alkali at a pH of at least 12, or with use of a usual acid, such as hydrochloric acid, sulfuric acid or the like. According to the preferable embodiment of the invention, the product is hydrolyzed by adding dropwise 10N sodium hydroxide to the enzyme-treated product in small portions over a period of about 15 minutes with stirring to obtain a thoroughly stirred mixture having a pH of at least 12, and heating the mixture at a temperature of 95° to 100° C. for about 60 minutes. The resulting mixture is cooled with ice and thereafter neutralized with a suitable acid, such as hydrochloric acid or sulfuric acid.

The desired substance is isolated from the resulting mixture and purified in a usual manner, for example, by filtration, centrifugation, gel filtration, desalting, or a combination of such procedures. Preferably gel filtration is conducted, for example, with use of Sephadex G-100, Toyopearl HW40 and Sephacryl S-200. Desalting can be carried out suitably, for example, by gel filtration with use of Sephadex G-15 or by membrane filtration with use of Millipore NMWL $10^3$ (product of Nippon Millipore Ltd., Japan).

The substance of this invention thus prepared is usually freeze-dried as a product and preserved at a low temperature of about 2° to 7° C. The substance is also sterilized suitably.

The present substance is used for medicinal purposes in the following manner. As already described, the substance has immunoactivity, namely activity to inhibit the multiplication of various microorganisms, such as protozoans, bacteria, viruses, etc. and anticancer activity against mouse leukemia P388. The substance is low in toxicity and effective as a drug for mammals including man and animals.

When the present substance is used for medicinal applications for man and animals, the substance is formulated into pharmaceutical compositions with use of pharmaceutically acceptable, non-toxic carriers. Various usual diluents or excipients are usable as carriers in accordance with the mode of application. Suitable pharmaceutically acceptable non-toxic carriers include but are not limited to water such as distilled water, salts solutions such as sodium chloride solution, alcohols, polyethylene glycols, ethoxylated isostearyl alcohol, polyoxyisostearyl alcohol, polyoxyethylene sorbit, sorbitan esters, gelatine, lactose, amylose, and the like. The pharmaceutical preparations can be sterilized and if desired mixed with auxiliary agents, such as solubilizing agents, buffers, analgesics, preservatives, stabilizers, emulsifiers, salts for influencing osmotic pressure, coloring agents, flavoring agents, etc. Other drugs can be incorporated into the compositions.

Although not limitative, such compositions are preferable in the form of parenteral preparations. For application, particularly suitable are injection solutions, as well as suspensions and emulsions. The injection can be given by a usual method, for example, intravenously singly or conjointly with a usual auxiliary solution of glucose, amino acid or the like. When desired, the injection can be administered singly intramuscularly, subcutaneously, intracutaneously or intraperitoneally. The compositions of this invention which are prepared in forms other than injections may be given orally or topically (e.g. as ointment).

The amount of the active component (present substance) in the composition and the dose thereof are suitably determined according to the method and form of administration, purpose and symptoms of the patient. In the case of an injection containing about 1 to about 80 W/V % of the active component, the injection is given at such a dose that about 1 to about 1000 mg/kg of body weight/day of the active component will be administered. The present composition need not be given once daily but can be given in three to four divided doses per day. Compositions in other forms may be given at suitable doses with reference to the above dosage of the injection.

The substance of this invention is tested pharmacologically as will be described below. I. Toxoplasma multiplication inhibition test The test is conducted according to the methods described in the following literature.

Jap. J. vet. Sci., 37, 235–243 (1975) and Zbl. Bakt. Hyg., I. Abt. Orig. A244, 374–382 (1979).

The specimens of present substance obtained in the examples to be described later are tested in canine monocytes, bovine monocytes, human heart cells, mouse kidney cells and mouse peritoneal macrophages which are prepared according to the methods described in the above literature. Tables 1 to 5 show the percentages of toxoplasma multiplication inhibition achieved in the cells, i.e. the percentages of the number of cells in which the number of toxoplasmas is 0, 1 to 5, or $\geq 6$, relative to the total test cells. The percentages of inhibition listed are represented by the following symbols.

| | |
|---|---|
| <10 | A |
| 10 to <20 | B |
| 20 to <30 | C |
| 30 to <40 | D |
| 40 to <50 | E |
| 50 to <60 | F |
| 60 to <70 | G |
| 70 to <80 | H |
| 80 to <90 | I |
| 90 to $\leq$100 | J |

TABLE 1

Inhibition of toxoplasma multiplication in canine monocytes

| Test No. | Specimen | substance Concn. (%) | Number of toxoplasmas in unit cell | | |
|---|---|---|---|---|---|
| | | | 0 | 1–5 | $\geq 6$ |
| 1 | Example 2 | 0.25 | I | B | A |
| 2 | Example 2 | 0.50 | J | A | A |
| 3 | Example 2 | 0.75 | J | A | A |
| 4 | Example 2 | 1.00 | J | A | A |
| 5 | Example 6 | 0.75 | I | B | A |
| 6 | Example 8 | 0.50 | J | A | A |
| 7 | Example 5 | 1.00 | H | B | B |
| 8 | Example 7 | 0.75 | F | C | B |
| 9 | Example 9 | 0.75 | G | C | B |
| 10 | Example 10 | 0.75 | G | C | B |
| 11 | Control* | 10 | D | C | D |

*Normal canine blood plasma.

TABLE 2

Inhibition of toxoplasma multiplication in bovine monocytes

| Test No. | Specimen | substance Concn. (%) | Number of toxoplasmas in unit cell | | |
|---|---|---|---|---|---|
| | | | 0 | 1–5 | $\geq 6$ |
| 1 | Example 2 | 0.25 | I | A | A |
| 2 | Example 6 | 0.25 | J | A | A |
| 3 | Example 8 | 0.50 | J | B | A |
| 4 | Example 5 | 0.50 | E | D | B |

TABLE 2-continued

Inhibition of toxoplasma multiplication in bovine monocytes

| Test No. | Specimen | substance Concn. (%) | Number of toxoplasmas in unit cell | | |
|---|---|---|---|---|---|
| | | | 0 | 1-5 | ≧6 |
| 5 | Example 7 | 1.00 | J | A | A |
| 6 | Example 9 | 0.75 | J | C | B |
| 7 | Example 10 | 0.75 | G | C | B |
| 8 | Control* | 10 | E | D | E |

*Normal bovine blood serum.

TABLE 3

Inhibition of toxoplasma multiplication in human heart cells

| Test No. | Specimen | substance Concn. (%) | Number of toxoplasmas in unit cell | | |
|---|---|---|---|---|---|
| | | | 0 | 1-5 | ≧6 |
| 1 | Example 2 | 0.75 | I | B | A |
| 2 | Example 6 | 1.00 | J | A | A |
| 3 | Example 8 | 0.50 | I | B | A |
| 4 | Example 5 | 0.50 | G | C | B |
| 5 | Example 7 | 0.50 | H | B | A |
| 6 | Example 9 | 0.75 | G | C | B |
| 7 | Example 10 | 0.75 | G | C | B |
| 8 | Control* | 10 | F | D | B |

*Normal bovine serum.

TABLE 4

Inhibition of toxoplasma multiplication in mouse kidney cells

| Test No. | Specimen | substance Concn. (%) | Number of toxoplasmas in unit cell | | |
|---|---|---|---|---|---|
| | | | 0 | 1-5 | ≧6 |
| 1 | Example 2 | 0.50 | J | A | A |
| 2 | Example 6 | 0.25 | J | A | A |
| 3 | Example 8 | 0.50 | J | A | A |
| 4 | Example 9 | 0.50 | I | B | B |
| 5 | Example 5 | 0.50 | G | C | B |
| 6 | Example 10 | 0.75 | I | B | A |
| 7 | Example 7 | 0.50 | G | C | B |
| 8 | Control* | 10 | E | D | E |

*Normal mouse serum.

TABLE 5

Inhibition of toxoplasma multiplication in mouse peritoneal macrophages

| Test No. | Specimen | substance Concn. (%) | Number of toxoplasmas in unit cell | | |
|---|---|---|---|---|---|
| | | | 0 | 1-5 | ≧6 |
| 1 | Example 2 | 0.25 | I | B | A |
| 2 | Example 5 | 0.50 | E | D | C |
| 3 | Example 7 | 0.50 | F | C | C |
| 4 | Example 6 | 1.00 | J | A | A |
| 5 | Control* | 10 | D | E | D |

*Normal mouse serum.

Tables 1 to 5 show that the substance of this invention effectively inhibits toxoplasma multiplication in homologous cells and in heterologous cells alike. II. Chemotherapy of experimental toxoplasmosis (acute)

BALB/c mice weighing about 18 to 20 g are divided into 3 groups of ten members and used for the chemotherapy of experimental toxoplasmosis. Each of the mice is intraperitoneally inoculated with an isotonic sodium chloride solution containing $5 \times 10^2/0.25$ ml of a virulent toxoplasma strain S-273. Twenty-four hours thereafter, 0.25 ml of saline is given to group I (control) once daily for 4 weeks. Acetylspiramycin (in solution) is orally given to group II (for comparison) at a dose of 0.2 g/kg of body weight/day once daily for 4 weeks.

The substance of the invention prepared in Example 6 is intraperitoneally given to group III (for this invention) once daily for 4 weeks at a dose of 1 mg/mouse, conjointly with the oral administration of 0.2 g/kg of body weight/day of acetylspiramycin.

On the 30th day postinfection, the serum autibody titer (according to the latex method) and the number of brain cysts (by plankton cytometer) are measured. The reduction of the cyst number is calculated from the following equation.

$$\text{Reduction (\%)} = \frac{A - B}{A} \times 100$$

wherein A is the number of brain cysts of the group I (control), and B is the number of brain cysts of group II or group III.

Nude mice of BALB/c strain are inoculated with the brain homogenates of the groups of mice, which are checked for the presence of toxoplasma in terms of the number of the resulting deaths. Table 6 shows the result.

TABLE 6

| Group | Cyst number (reduction, %) | | +HA titer value | Antibody % | Number of dead nude mice |
|---|---|---|---|---|---|
| I (Control) | 4302 | — | 10/10 | 100 | 16/16 |
| II (Comparison) | 26 | (99.4) | 7/8 | 87.5 | 14/14 |
| III (Invention) | 0 | (100) | 0/10 | 0 | 0/13 |

Table 6 reveals that the mice acutely infected with toxoplasma are difficult to completely cure by the administration of acetylspiramycin only (group II). Although the mean number of brain cysts has decreased greatly as compared with the control (group I), all the 14 nude mice inoculated with the brain homogenate die. This indicates the presence of toxoplasma. In contrast, the use of the substance of the invention (group III) reduces the cyst number to 0, while 13 nude mice inoculated with the brain homogenate all survive, indicating the absence of toxoplasma. Thus the toxoplasmosis can be cured completely. III. Chemotherapy of experimental toxoplasmosis (chronic)

BALB/c mice in 4 groups of 10 members each are intraperitoneally given 0.5 ml of saline containing $10^2$ low virulent toxoplasmas (S-273 strain). Four weeks postinfection, the mice are inoculated again with 0.5 ml of the same saline. Four weeks thereafter, the mice are given the substance of the invention obtained in Example 6 and acetylspiramycin each singly or in combination, daily for 4 weeks. A control group is also prepared to which neither of the drugs is given. When the present substance is used singly, 0.5 ml of saline containing 20 mg of the substance is administered intraperitoneally. When acetylspiramycin is given singly, 0.5 ml of saline containing 8 mg of the drug is administered orally. For the conjoint administration of these drugs, the same quantities of the same solutions as above are given simultaneously by the same methods are above.

The effects achieved are evaluated in terms of the number of brain cysts, reduction (%) thereof and antibody titer which are determined on completion of the administration of the drugs in the same manner as above. Table 7 shows the results.

TABLE 7

| Group | Brain cysts Number | Reduction (%) | Antibody titer |
|---|---|---|---|
| I (control) | 1608.90 | — | 1:128–1:512 |
| II (comparison, acetylspiramycin only) | 1052.15 | 34.61 | 1:128–>1:512 |
| III (present substance only) | 1061.43 | 32.91 | 1:256–>1:512 |
| IV (combination) | 765.79 | 52.40 | ≧1:512 |

Table 7 shows that the mean cyst number of about 1609 for the control (group I) can be decreased to an average of 1061 by the single administration of the present substance (group III) and to an average of 766 by the conjoint use of the substance and acetylspiramycin (group IV). The reduction achieved by the conjoint use is more than about 50%. This indicates that the present substance has immunoactivity to produce a therapeutic effect on the cysts of mice chronically infected with toxoplasma.

IV. Antibacterial activity in macrophages (1) Gram-positive bacteria (*Bacillus subtilis* H IAM 1521) or gram-negative bacteria (*Escherichia coli* B wild type or *Proteus vulgaris* HX 19) are caused to act for 30 minutes on peritoneal macrophages obtained from a normal mouse and incubated for 24 hours in TC-199 medium containing 10% fetal calf serum. The bacterial of each type are used in 50 times the amount of the macrophages (Experiment A). The macrophages are further incubated for 2 hours in the same medium in the presence of 0.75 mg/ml of the present substance obtained in Example 6 (Experiment C). The same procedure as above Experiment C is repeated for a control test without using the present substance (Experiment B). The number of bacteria remaining in the macrophage is counted with reference to dye specimens. Table 8 shows the results.

TABLE 8

| Number of bacteria in macrophages | Exp. A (0 hour) | | Exp. B (In 2 hrs.) | | Exp. C (In 2 hrs.) | |
|---|---|---|---|---|---|---|
| *E. coli* | | | | | | |
| 0 | 0 | (%) | 1.3 | (%) | 2.7 | (%) |
| 1–10 | 9.7 | | 33.6 | | 56.9 | |
| 11–20 | 29.7 | | 36.0 | | 28.8 | |
| 21–30 | 24.6 | | 17.3 | | 7.7 | |
| ≧31 | 36.0 | | 11.7 | | 4.0 | |
| *P. vulgaris* | | | | | | |
| 0 | 32.0 | (%) | 36.2 | (%) | 50.5 | (%) |
| 1–10 | 59.3 | | 57.3 | | 41.8 | |
| 11–20 | 4.2 | | 3.0 | | 5.0 | |
| 21–30 | 2.7 | | 2.2 | | 1.3 | |
| ≧31 | 1.8 | | 1.3 | | 1.3 | |
| *B. subtilis* | | | | | | |
| 0 | 0 | (%) | 1.2 | (%) | 3.2 | (%) |
| 1–10 | 9.5 | | 29.2 | | 34.7 | |
| 11–20 | 18.5 | | 37.2 | | 33.5 | |
| 21–30 | 22.8 | | 21.2 | | 19.3 | |
| ≧31 | 49.2 | | 11.3 | | 9.3 | |

Table 8 reveals that the substance of the invention is effective for inhibiting multiplication of gram-positive and gram-negative bacteria in pertitoneal macrophages of normal mice.

(2) Incubated macrophages are prepared by repeating the proceudre of Experiment C above except that the macrophages are cultured for 4 hours in the same medium in the presence of 0.75 mg/ml of the present substance obtained in Example 6. The macrophages are broken down in distilled water and thereafter incubated on a flat plate. The number of live *E. coli* cells remaining in the macrophages is counted. The same procedure as above is repeated for a control test in the absence of the present substance.

Figure 3:
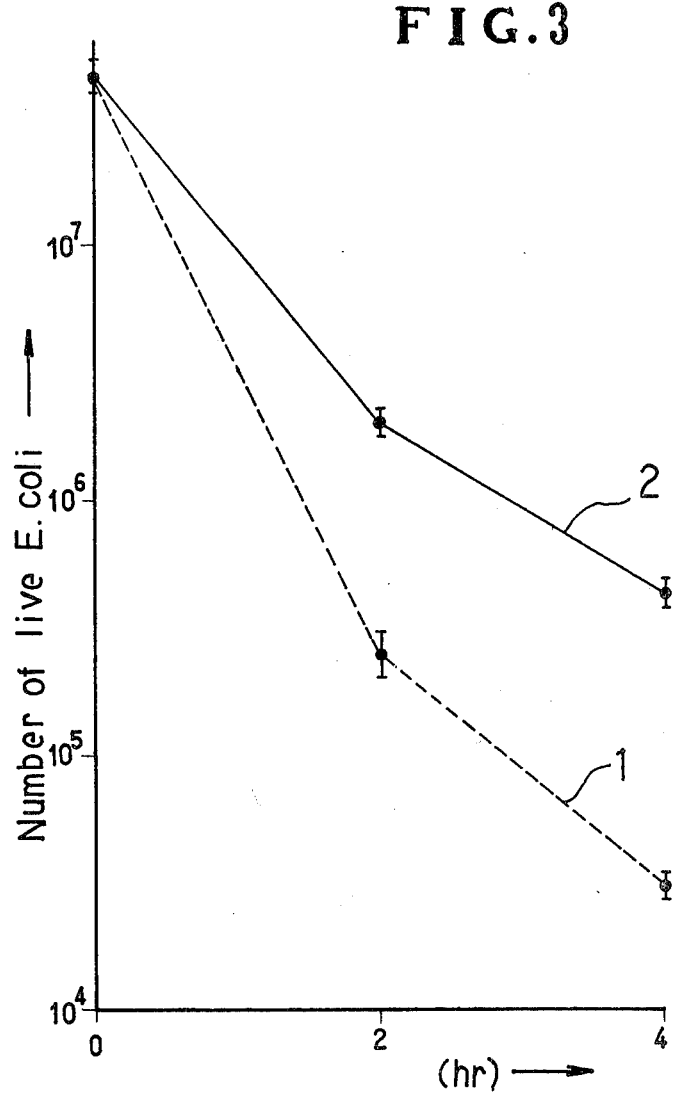

FIG. 3 shows the results. Line (1) shown represents the result achieved with use of the present substance, and line (2) the result of the control test.

Like Table 8, the drawing reveals that the present substance remarkably inhibits the multiplication of *E. coli* in peritoneal macrophages of normal mice.

V. Inhibition of multiplication of virus

The substance of this invention prepared in Example 6 is dissolved in Eagle's minimum essential medium (see "Igaku no Ayumi (Progress of Medicine)", 62, No. 6, Aug. 5, 1967) to a concentration listed in Table 9, and the solution is filtered with a 0.45 μm membrane filter (product of Nippon Millipore Ltd.) to sterilize. Two ml of the solution is added to HEP-2 cells ($10^6$ cells/plate) derived from human epitherial laryngeal cancer and incubated for 2 days. The cells are then infected with 2 PFU (plaque formation unit)/cell of Herpes simplex virus type II (186 strain), incubated at 37° C. for 18 hours and thereafter cooled to −80° C. to terminate the reaction. The number of viruses is counted. The same procedure as above is repeated except that HEP-2 cells are infected with 0.2 PFU/cell of Herpes simplex virus type II (186 strain) and then incubated at 37° C. for 25 hours. Control groups are also prepared without using the present substance. Table 9 shows the results.

TABLE 9

| Conc. of present substance (mg/ml) | Reproduction of viruses (PFU × $10^4$/$10^5$ cells) | |
|---|---|---|
| | 2 PFU/cell | 0.2 PFU/cell |
| 0 (control) | 196.0 ± 9.5 | 192.0 ± 36.0 |
| 1 | 157.0 ± 3.0(P<0.001) | 121.0 ± 6.0(P<0.001) |
| 5 | 94.0 ± 9.0(P<0.001) | 38.0 ± 2.0(P<0.001) |
| 10 | 9.8 ± 0.7(P<0.001) | 9.7 ± 1.7(P<0.001) |

The significant difference P listed in Table 9 is determined by Student's t-test. The table reveals that the present substance significantly inhibits the multiplication of the virus at concentrations of 1 to 10 mg/ml.

VI. Anti-mouse leukemia P388

A 0.1 ml quantity of saline containing $10^6$ cells of mouse leukemia P388 is intraperitoneally transplanted in each of 10-week-old male $BDF_I$ mice at a middle portion of its stomach on the right side thereof.

Consecutively for 9 days following the transplant, the present substance obtained in Example 6 and 1-(2-tetrahydro)-5-fluorouracil (Ftorafur, FT207, product of TAIHO Pharm. Co., Ltd., Japan) are intraperitoneally injected into the same portion singly or conjointly.

The present substance is given once daily at a dose of 3.0 mg/0.1 ml saline/10 g body weight, and Ftorafur 207 once daily at dose of 1.0 mg/0.1 ml saline/10 g body weight.

No drug is given to a control group.

The anticancer effect is evaluated in terms of survival rate as calculated at the time when all the mice of each group have died, as compared with the control group. Table 10 below shows the results.

TABLE 10

| Group | No. of mice | Number of days of survival of each mouse | Mean number of days of survival | Survival rate (%) | Mean wt. (g) before transplant |
|---|---|---|---|---|---|
| Control | 7 | 9, 9, 10, 10, 10, 10, 11 | 9.86 ± 0.69 | 0 | 25.86 |
| Present substance 300 mg/kg | 7 | 11, 11, 12, 12, 12, 12, 13 | 11.86 ± 0.69 | 20.29 | 26.14 |
| Ftorafur 100 mg/kg | 7 | 12, 12, 13, 13, 14, 15, 16 | 13.57 ± 1.51 | 37.68 | 26.14 |
| Ftorafur 100 mg/kg + present substance 300 mg/kg | 7 | 16, 17, 18, 18, 18, 19, 20 | 18.00 ± 1.29 | 82.61 | 25.86 |

The above table reveals that the present substance achieves an effect against mouse leukemia P388 even if given singly and exhibits a synergistic effect when used conjointly with the known drug.

VII. Acute toxicity

The present substance is tested for acute toxicity by the method of Litchfield and Wilcoxon (J. Pharmacol. Exp. Ther., 90, 99, 1949), using BALB/c female mice.

No deaths result when the substance is given at a dose of 4,000 mg/kg intraperitoneally or 2,000 mg/kg intravenously. Accordingly the $LD_{50}$ of the substance is larger than 4,000 mg/kg intraperitoneally or larger than 2,000 mg/kg intravenously.

Given below are reference examples in which starting materials are prepared for the production of the biologically active substance of the invention.

Reference Example 1

Each of 5 beagles, 10 kg in mean body weight, is intraperitoneally inoculated with $10^6$ toxoplasmas (Toxoplasma gondii). In the 5th week postinoculation, the animal is inoculated again with $10^6$ toxoplasmas of the same strain to prepare a toxoplasma-hyperimmune dog. In the 2nd week after the second inoculation, TLA is intravenously injected into the dog at a dose of 10 μg/kg body weight. The blood is collected 24 hours after the injection.

The blood plasma thus obtained has an antibody titer of at least 1:1000 in terms of Sabin-Feldman dye titer or at least 1:4000 as determined by the indirect immunofluorescence method. Immunoglobulin G (Ig G) antibody only is detected.

Reference Examples 2 and 3

The procedure of Reference Example 1 is repeated except that TLA is replaced by Con A or PHA.

The blood plasma obtained in each case has the following antibody titer.

| Dye titer: | at least 1:1000 |
|---|---|
| Indirect immunofluorescence method: | at least 1:4000 |

(Ig G antibody only is detected.)

Reference Example 4

The procedure of Reference Example 1 is repeated except that Toxoplasma gondii and TLA is replaced by Piroplasmea (Babesia gibsoni) and BLA, respectively, to obtain blood plasmas from Piroplasmea-hyperimmune dogs. The antibody titer of the blood plasma is at least 1:1000 as determined by the indirect immunofluorescence method.

Reference Example 5

Each of 6-month-old calves is given $2.5 \times 10^8$ toxoplasmas (Toxoplasma gondii) by cervical intramuscular inoculation. In the 5th week postinoculation, the animal is inoculated again with $5 \times 10^8$ toxoplasmas of the same strain. In the 2nd week after the second inoculation, TLA is intravenously injected into the calf at a dose of 1 μg/kg body weight. The blood is collected 24 hours after the injection to obtain serum. The serum has a latex agglutination titer of at least 1:2048.

Reference Example 6

The procedure of Reference Example 5 is repeated except that Toxoplasma gondii and TLA is replaced by Piroplasmea (Babesia spp.) and BLA, respectively to obtain sera from Piroplasmea-hyperimmune calves. The sera have antibody titers (indirect immunofluorescence method) of 1:256–1000.

Reference Example 7

Each of mice is intraperitoneally inoculated with $1 \times 10^6$ toxoplasmas (Toxoplasma gondii, low virulent strain). In the 5th week postinfection, the mouse is inoculated again with $1 \times 10^6$ toxoplasmas of the same strain. In the 2nd week after the second inoculation, TLA is intraperitoneally injected into the mouse at a dose of 10 μg/kg body weight. The blood is collected from the toxoplasma hyperimmune mouse 24 hours after the injection to obtain serum, which has an antibody titer (indirect immunofluorescence method) of at least 1:4000.

Reference Example 8

The procedure of Reference Example 7 is repeated except that Toxoplasma and TLA is replaced by Piroplasma (Babesia rhodhaini) and BLA, respectively to obtain sera from Piroplasmea-hyperimmune mice. The serum has antibody titers (indirect immunofluorescence method) of at least 1:4000.

Reference Example 9

The procedure of Reference Example 7 is repeated except that Toxoplasma and TLA is replaced by Haemosporidia (Plasmodium berghei NK strain) and MLA, respectively to obtain serum from Haemosporidia-hyperimmune mice. The serum has antibody titers (indirect immunofluorescence method) of at least 1:1000.

Reference Example 10

Spleen cells from a toxoplasma-hyperimmune mouse are washed twice with heparinized HBSS (containing 10 units/ml of heparin) by centrifugation. The sediment is suspended in TC-199 medium containing 20% heat-inactivated calf serum (HICS) and antibiotics (100 units of penicillin G and 100 μg of dihydrostreptomycin per ml of the medium) to cause the medium to contain $1\times10^7$ cells/ml. With addition of 50 μg/ml of TLA to the medium, the cells are incubated at 37° C. for 48 hours. A supernatant is separated from the resulting culture by centrifugation at 4° C. and at 3,000 rpm for 30 minutes.

Reference Example 11

The spleen in removed from a normal mouse, and spleen cells are separated off by the Conray-Ficoll method and washed twice with heparinized HBSS (10 units heparin/ml) by centrifugation. The sediment is suspended in TC-199 medium containing 20% heat-inactivated calf serum (HICS) and antibiotics (100 units of penicillin G and 100 μg of dihydrostreptomycin per ml of the medium) to cause the medium to contain about $10^7$ cells/ml. With the addition of 66 V/V % of the culture supernatant obtained in Reference Example 10, the cells are incubated for 3 weeks. A ⅓ portion of the medium is refreshed every three days. After the completion of incubation, the culture is washed with heparinized HBSS (10 units heparin/ml), and 100 μg/ml of TLA is added to the culture. The cells are further incubated at 37° C. for 48 hours. A supernatant is separated from the resulting culture by centrifugation at 4° C. and at 3,000 rpm for 30 minutes.

Reference Example 12

A culture supernatant is obtained in the same manner as in Reference Example 11 except that 100 μg/ml of TLA is substituted for the supernatant of Reference Example 10.

Examples are given below in which the present substance is prepared.

EXAMPLE 1

A 0.1 g quantity of pronase (Pronase P, product of Kaken Chemical Co., Ltd., Japan) is added to a 100-ml portion of the blood plasma obtained in Reference Example 1, and the plasma is treated with the enzyme in an incubator at 37° C. for 12 hours with stirring. The mixture is then heated to inactivate the enzyme and thereafter cooled with ice water.

The enzyme-treated plasma is subjected to gel filtration with Sephacryl S-200 using 18.6 ml/hr of 0.01 M phosphate buffer solution having a pH of 7.2 to obtain a toxoplasma inhibitory active fraction.

The crude fraction is further subjected to gel filtration with Toyopearl HW40, and the resulting active fraction is desalted with Sephadex G-15 (1.2 cm×40 cm column) using redistilled water, giving 0.6 g of the substance of this invention having the physicochemical and biological properties already described. The substance is sterilized by filtration, freeze-dried and preserved at 4° C.

EXAMPLE 2

Another portion of the bood plasma obtained in Reference Example 1 is treated with an enzyme in the same manner as in Example 1.

To a 100 ml portion of the resulting plasma is added 10 ml of 10N NaOH with stirring, and the mixture is further continuously stirred at 90° to 100° C. for 60 minutes and then cooled. A 10 ml quantity of 10N HCl is added to the mixture to adjust the pH to 7.0. The mixture is then filtered with Toyo Filter Paper No. 5C (product of Toyo Roshi Co., Ltd., Japan). The filtrate is centrifuged at 10,000 rpm for 20 minutes to collect a supernatant.

The supernatant is subjected to gel filtration with Sephacryl S-200 (0.9 cm×90 cm column) by passing 0.01M phosphate buffer solution of pH 7.2 through the column at a rate of 18.6 ml/hr to obtain a crude fraction.

The crude fraction is further subjected to gel filtration with Toyopearl HW40. The resulting active fraction is desalted with Sephadex G-15 (1.2 cm×40 cm column) using redistilled water, giving 0.54 g of the present substance having the foregoing physicochemical and biological properties. The substance is sterilized by filtration, freeze-dried and preserved at 4° C.

EXAMPLES 3-13

The substance of this invention is prepared in the same manner as in Example 2 with the exception of using the blood plasma, serum or supernatant (100 ml) prepared in Reference Examples 2-12.

| Ex. No. | Ref. Ex. No. for starting material (origin) |
|---|---|
| 3 | 2 (Toxoplasma-hyperimmune beagle) |
| 4 | 3 (Toxoplasma-hyperimmune beagle) |
| 5 | 4 (Piroplasmea-hyperimmune beagle) |
| 6 | 5 (Toxoplasma-hyperimmune calf) |
| 7 | 6 (Piroplasmea-hyperimmune calf) |
| 8 | 7 (Toxoplasma-hyperimmune mouse) |
| 9 | 8 (Piroplasmea-hyperimmune mouse) |
| 10 | 9 (Haemosporidia-hyperimmune mouse) |
| 11 | 10 (Toxoplasma-hyperimmune mouse spleen cells) |
| 12 | 11 (normal mouse spleen cells) |
| 13 | 12 (normal mouse spleen cells) |

The substance obtained in each of the examples is identical with the one obtained in Example 2 in repsect of physical, chemical and biological properties.

The substance obtained in Example 6 is further tested for solubility in organic solvents by the following method.

A 100 mg quantity of the substance is added to 5 ml of an organic solvent, and the mixture is shaken for 30 minutes and then centrifuged for 10 minutes at 3000 rpm to separate the mixture into a supernatant fraction and an insoluble fraction. Each of the fractions are then dried, and 1 ml of pure water is added to the dried product to determine the total nitrogen weight. The same procedure as above is repeated with use of other organic solvents. The results are as follows.

|  | Supernatant fraction (μg) | Insoluble fraction (μg) | Supernatant (%) |
|---|---|---|---|
| Ethanol | 2.10 | 56.06 | 3.6 |
| Methanol | 49.41 | 6.72 | 88.0 |
| Ether | 0.01 | 59.75 | 0 |
| Benzene | 0.02 | 58.75 | 0 |
| Chloroform | 1.72 | 63.79 | 2.6 |
| Acetone | 0.14 | 66.91 | 0.2 |

EXAMPLE 14

The present substance is prepared in the same manner as in Example 2 except that pronase is replaced by the same amount of papain (product of Wako Pure Chemical Industries, Ltd., Japan). The substance is identical with the one obtained in Example 2 in properties.

EXAMPLE 15

The present substance is prepared in the same manner as in Example 2 except that pronase is replaced by the same amount of chymotripsin (product of Miles-Feravac., Ltd.). The substance is identical with the one obtained in Example 2 in properties.

We claim:

1. A biologically active glycoprotein having a molecular weight of 3,000 to 5,000 as determined by a gel filtration method and has activity to inhibit toxoplasma multiplication not only in homologous cells but also in heterologous cells, and further has the following physical and chemical properties;
   (a) solubility: freely soluble in water and practically incoluble in methanol, ethanol, ether, benzene, chloroform and acetone;
   (b) ratio of sugar and protein contents: protein 85-90%, hexosamine 9-13% and hexose 1-2% calculated as glucose;
   (c) constituent amino acid of protein portion: aspartic acid, threonine, serine, glutamic acid, glycine, alanine, cystine, valine, methionine, isoleucine, leucine, tyrosine, phenylalanine, lysine, tryptophan, histidine, arginine and proline;
   (d) aspartic acid, glutamic acid and lysine contents in total amino acids: 45 to 65% by weight;
   (e) pH: 7.0 to 7.2 (1 W/V % aqueous solution);
   (f) thermal stability: when 1 W/V % aqueous solution of the substance is heated at $60\pm0.1°$ C. for 30 minutes, the solution still retains the immunoactivity to inhibit toxoplasma multiplication in homologous cells and heterologous cells;
   (g) IR absorption: characteristic absorption at the following wave number $(cm^{-1})$; 3600-2900 (strong), 1700-1500 (strong), 1440-1380 (medium), 1160-1080 (medium), and 550 (medium);
   (h) UV absorption: maximum absorption is found at 274-276 nm for 0.1 W/V % aqueous solution;
   (i) color reaction; positive Lowry-Folin process, Ninhydrin reaction, Phenol-sulfuric acid reaction and Elson-Morgan's reaction;
   (j) color and appearance: white and amorphous.

2. An immunoactive composition comprising as an active ingredient an immununoactivating effective amount of a biologically active substance in admixture with a pharmaceutically acceptable, non-toxic carrier, the substance being a glycoprotein having a molecular weight of 3,000 to 5,000 as determined by a gel filtration method and having activity to inhibit toxoplasma multiplication not only in homologous cells but also in heterologous cells, and further having the following physical and chemical properties;
   (a) solubility: freely soluble in water and practically insoluble in methanol, ethanol, ether, benzene, chloroform and acetone;
   (b) ratio of sugar and protein contents: protein 85-90%, hexosamine 9-13% and hexose 1-2% calculated as glucose;
   (c) constituent amino acid of protein portion: aspartic acid, threonine, serine, glutamic acid, glycine, alanine, cystine, valine, methionine, isoleucine, leucine, tyrosine, phenylalanine, lysine, tryptophan, histidine, arginine and proline;
   (d) aspartic acid, glutamic acid and lysine contents in total amino acids: 45 to 65% by weight;
   (e) pH: 7.0 to 7.2 (1 W/V % aqueous solution);
   (f) thermal stability: when 1 W/V % aqueous solution of the substance is heated at $60\pm0.1°$ C. for 30 minutes, the solution still retains the immunoactivity to inhibit toxoplasma multiplication in homologous cells and heterologous cells;
   (g) IR absorption: characteristic absorption at the following wave number $(cm^{-1})$; 3600-2900 (strong), 1700-1500 (strong), 1400-1380 (medium), 1160-1080 (medium), and 550 (medium);
   (h) UV absorption: maximum absorption is found at 274-276 nm for 0.1 W/V % aqueous solution;
   (i) color reaction; positive Lowry-Folin process, Ninhydrin reaction, Phenol-sulfuric acid reaction and Elson-Morgan's reaction;
   (j) color and appearance: white and amorphous.

3. Method of inhibiting the multiplication of protozoans in heterologous cells as well as in homologous cells comprising administering an effective amount of the composition as defined in claim 2 to a host infected with the protozoans.

4. Method of inhibiting the multiplication of bacteria comprising administering an effective amount of the composition as defined in claim 2 to a host infected with bacteria.

5. Method of inhibiting the multiplication of viruses comprising administering the composition as defined in claim 2 to a host infected with viruses.

6. Method of treating mouse leukemia P388 comprising administering the composition as defined in claim 2 to a host having said leukemia.

7. An immunoactive composition as defined in claim 2 which is in the form of an injection comprising an immunoactivating effective amount of the biologically active substance in admixture with a pharmaceutically acceptable, non-toxic carrier suitable for administration by injection.

8. An immunoactive composition as defined in claim 2 or 7 which comprises the biologically active substance in an amount effective for inhibiting the multiplication of protozoans.

9. An immunoactive composition as defined in claim 2 or 7 which comprises the biologically active substance in an amount effective for inhibiting the multiplication of bacteria.

10. An immunoactive composition as defined in claim 2 or 7 which comprises the biologically active substance in an amount effective for inhibiting the multiplication of viruses.

* * * * *